United States Patent [19]

Heckel

[11] Patent Number: 5,520,529
[45] Date of Patent: May 28, 1996

[54] DEVICE FOR PRODUCING A MATERIAL FOR ORTHOPEDIC PURPOSES

[75] Inventor: Gerd Heckel, Mötzingen, Germany

[73] Assignee: Carbontec GmbH, Gesellschaft zur Anwendung von Faserverbundwerkstoffen, Rottenburg Ergenzingen, Germany

[21] Appl. No.: 298,306

[22] Filed: Sep. 1, 1994

[51] Int. Cl.[6] .................................................. B29C 35/00
[52] U.S. Cl. .............................. 425/218; 264/83; 425/394
[58] Field of Search ............................. 425/84, 218, 458, 425/383, 394, 406; 264/83

[56] References Cited

U.S. PATENT DOCUMENTS

| 921,067 | 5/1909 | Bentley | 425/84 |
|---|---|---|---|
| 2,061,497 | 11/1936 | Beauchamp | 425/218 |
| 3,096,545 | 7/1963 | Rowland | 425/394 |
| 3,736,088 | 5/1973 | Jimenez | 425/218 |
| 4,030,873 | 6/1977 | Morrison | 425/218 |
| 4,501,544 | 2/1985 | Akutagawa | 425/218 |
| 4,902,215 | 2/1990 | Seemann, III | 425/389 |
| 4,946,360 | 8/1990 | Brown | 425/458 |
| 5,244,375 | 9/1993 | Laurence et al. | 425/406 |

FOREIGN PATENT DOCUMENTS

| 53176 | 4/1942 | Netherlands | 425/218 |
|---|---|---|---|
| 1296427 | 3/1987 | U.S.S.R. | 425/218 |

*Primary Examiner*—Robert Davis
*Attorney, Agent, or Firm*—Browdy and Neimark

[57] ABSTRACT

A shapeable and re-shapeable material for orthopedic devices is formed of an amorphous, thermoplastic forming a matrix layer, for example of PMMA which is polymerized at room temperature, and of reinforcing fibers inserted therein. It is possible to provide several matrix layers, bonded in a laminate-like manner, respectively provided with fibers. The material can be deformed in the course of producing orthopedic devices and can be re-deformed in the course of using the device by being respectively heated to less than 200° C. A mixture of the reaction components of the plastic material is placed in a mold for producing the shapeable material, the fibers are placed on it and the polymerizing plastic material is compacted. Additional mixture and additional fibers can be added during the polymerization of the first matrix layer in the same manner to form further layers of the laminate-like shapeable material. The shapeable material is used for self-supporting, shell-like structures, particularly in orthopedic technology.

11 Claims, 1 Drawing Sheet

DEVICE FOR PRODUCING A MATERIAL FOR ORTHOPEDIC PURPOSES

FIELD OF INVENTION

The present invention relates to a material, in particular for orthopedic purposes, a process for producing such a material, in particular for orthopedic purposes, a device for executing such process and a use of such material.

BACKGROUND OF INVENTION

Materials wherein a matrix of plastic has been reinforced by inserted fibers have been used for the production of orthopedic devices for some time. For various reasons, plastic materials are better suited than the previously used customary materials such as plaster, leather or metals, because they are lighter, more permanent, less sensitive to moisture, more compatible with the skin and can be more easily made into the desired shape.

Up to now, thermosetting resins have generally been used as materials for the matrix of orthopedic devices. The disadvantage of these materials for orthopedic devices, with and without fibers, is that even though they can be made into the shape desired for the orthopedic device without problems, after curing they cannot be plastically deformed again. In this way such orthopedic devices are no longer optimal, because it is not possible to perfect their shape after experimental use or to adapt them to anatomical changes or new requirements over time.

For this reason, a material which was constructed in a sandwich-like manner and had outer layers of a thermosetting plastic material, between which a core of thermoplastic material was located, was also used for producing orthopedic devices which can be re-deformed. When shaping these materials, the thermosetting outer layers are only elastically deformed, while the core is plastically deformed. The plastically deformed core then maintains the elastically deformed outer layers in a pre-stressed position. Re-deformation is always possible by again heating and plastically deforming the core, in the course of which it is necessary to take the elastic limits of the outer layers into consideration.

However, orthopedic devices made of this sandwich-like material also have a considerable disadvantage. Further tension, caused when using the orthopedic devices, is added to the tension caused by shaping of the outer layers. The sum of these tensions must, of course, not exceed the permissible tension of the material, as a result of which only comparatively low tension in use can be permitted.

It must furthermore be taken into consideration that because of their sandwich-like configuration the layers of material form a shear connection with a high degree of rigidity with a high modulus in flexure E. Since it is generally true in the elastic range that deformations, i.e. displacements f, correspond to the quotient of tension/modulus of flexure, a high modulus of flexure in any event results in small displacements. It is furthermore true that in the same way that the sum of shaping tension and use tension is not allowed to exceed the permissible tension, the sum of shaping displacement f(D) and the displacement by use f(G) is not allowed to exceed the permissible displacement f(ZUL). Therefore, $$f(D)=f(XUL)-f(G).$$

applies for the just permissible shaping displacement.

Because of these relationships of the deformations, only a small shaping displacement f(G) is the result—depending on the necessary displacement by use f(G)—, which may be undesirable, depending on the type of the orthopedic device.

For this reason it was attempted to employ fiber-reinforced, partially crystalline thermoplastic materials for producing orthopedic devices. In contrast to the sandwich-like materials, partially crystalline thermoplastic materials permit sufficient deformation by use. In addition they also can be plastically deformed repeatedly, in contrast to the above mentioned thermoserring plastics, if they are heated to the appropriate temperature. However, they have two disadvantages which make their use problematical, particularly for orthopedic devices. First, the partially crystalline thermoplastic materials must be pressed after deformation, which is hardly possible with orthopedic devices; and secondly, the temperature range in which these plastic materials act in a thermoplastic manner is very narrow. If the temperature falls below this range, the plastic material can no longer be plastically deformed, if the temperature rises above above this range, the material melts. The upper limit and the lower limit of the temperature range only differ by approximately 5° C. It is easy to understand that staying within this temperature is hardly possible, so that the material cannot be plastically deformed in a simple manner.

SUMMARY OF INVENTION

Based on this state of the art, objects of the invention therefore include:

(a) producing a material of the type mentioned above, which material is easily deformed and can be redeformed in an easy way and which allows sufficient deformation;

(b) a process for producing such a material;

(c) a device for executing such process; and (d) a method of using such material.

The material of the invention consists essentially of a matrix layer of an amorphous, thermoplastic material which can be deformed in a simple manner, which can be redeformed any number of times respectively following heating, and of fibers, or tows or yarns of such fibers, which are impregnated with the plastic material or reinforce it and are embedded in it in layer form.

The advantage attained with this resides in that it is possible to produce orthopedic devices with the novel material which permit sufficient elastic deformation by use and which can be perfectly adapted in a simple manner, since it is possible to improve the original shaping by re-deformation following an experimental use; in addition, the service life of orthopedic devices can be increased by using the novel material, because of the re-deformation capability of the material it is possible to adapt the devices to anatomical changes instead of replacing them by new devices, as was necessary before. Shaping can either take place immediately during production by means of in situ techniques or following an intermediate step from a semi-finished mold, for example from a plate or a preform.

Polymethyl methacrylate (PMMA) is a suitable amorphous thermoplastic material for the matrix layers, which can be re-deformed when heated to 170° C. to 180° C. This temperature can be generated by means of any arbitrary heat source, best with a hot air blower or in a hot cabinet. The thermoplastic material selected should have a shear modulus (G) between 1 and 10 Newton/mm$^2$ in the heat softened state, or at least between 1 and 5 N/mm$^2$.

It is preferred that the amorphous thermoplastic material selected be one which is sufficiently soft over a range of at least 8° C. so that the matrix layer can be easily re-formed at any temperature within such 8° C. range.

In many cases the material is plate-shaped. It can have a single matrix layer with an enclosed layer of fibers. Depending on the anticipated stress, however, it may be advantageous to construct the material of several matrix layers; in most cases all of the additional matrix layers are reinforced with fibers. The matrix layers reinforced with the fibers embedded in layers form a laminate-like material and make transitions into each other in their border areas, which will be explained later in the course of the description.

Depending on the intended use, the fibers can be employed as layments in knitted, woven or net form; particularly with layments and woven forms, the fibers or yarns of different matrix layers which are essentially located in parallel planes can be differently oriented. Best suited are fibers in a web-like, easily cut form. If the material is only partially highly stressed, it is possible to cover only individual areas of the matrix layers with fibers. In the process the fibers can be oriented to correspond to the stress. If, for example, the material is primarily stressed in one direction, appropriately oriented fibers are used. But if a material which can be stressed in all directions in the plate direction of the material is needed, the fibers are used appropriately non-oriented, which results in a quasi isotropic material. The fibers, tows or yarns of all layers are impregnated and held together by the plastic material of the matrix layers.

All types and mixtures of commercially available fibers are suitable for the novel material, such as carbon fibers, glass fibers and ceramic fibers. Carbon fibers are very suitable and are often used. By using comparatively stiff fibers a material is obtained, with which it is possible to achieve a certain memory effect; this means that a deformed part returns to its original shape under the effect of heat, which can be useful, among other things, for correcting wrong shapes.

In view of protecting the material during transport and storage and in view of processing the material, in particular by gluing, it has been shown to be particularly advantageous to provide a cover layer for one or both outer surfaces of the material which adheres to the respective matrix layer. As will be explained further below, such a cover layer is preferably permeable in view of producing the material.

In general, the cover layer is flexible and is formed by a perforated foil or woven plastic material, for example.

The process for manufacturing the novel material can be performed in a simple manner. The reaction components of the plastic material for the matrix layer are mixed and placed in or on a mold as a viscous mixture; the fibers, or tows or yarns thereof, are placed on the matrix layer being created in this way; finally, polymerization of the mixture over several hours takes place to form the plastic material or matrix layer at a suitable temperature and in an oxygen-containing environment, generally air. The PMMA already mentioned is particularly suited because it is polymerized at a temperature between approximately 20° C. and 25° C., i.e. at a usual room temperature, so that it is possible to operate at an ambient temperature and the mold needs to be neither heated nor cooled.

A particularly good and homogeneous material is obtained if the matrix layer is levened out and compacted after the fibers have been placed on it but before or at the start of their polymerization. In the process the fibers are pushed into the matrix layer or the not yet polymerized, viscous material enters through the spaces between the fibers at their top, so that at the end the fibers are embedded into the plastic material of the matrix layer and are also maintained in their configuration because of this.

In order to obtain a material which can stand up to increased stresses, it is possible to place an additional viscous mixture of the reaction components of the plastic material on the lowest polymerized layer, if required with embedded fibers, which subsequently is polymerized into a matrix together with a first layer. In this way a laminate-like material is obtained wherein, however, the individual layers do not adhere to each other but make a transition into each other at their border areas as a result of their practically simultaneous polymerization, so that there are no layer boundaries and therefore no danger of de-lamination.

It is of course possible in this way to create additional matrix layers as desired, until the material has attained the required strength.

In general, as explained above in respect to the first matrix layer, these additional matrix layers are also covered with fibers, evened out and compacted, so that the fibers are embedded in the plastic material. In order to obtain a quasi isotropic material which can be equally stressed on all sides, the fibers of different matrix layers can be oriented in different directions, as described above. As already mentioned, all layers of the fibers are held together by the plastic material.

Following the layered construction of the material, another compacting can be performed under pressure. Prior to this and as described above, the material can be provided with a permeable cover layer which adheres to it and protects its surface prior to processing of the material. This advantageously flexible cover layer, for example a woven plastic material or a perforated foil, is placed on the outermost matrix layer prior to or at the start of polymerization and is bonded with it under pressure. The oxygen required for polymerization is taken from the air present in the cover layer or between the fibers of the web or in the perforations.

Although in general sufficient oxygen has access to the polymerization area through the permeable cover layer, it may be necessary in case of a great oxygen demand to exert the pressure on the upper layer of the material, which can be approximately 0.1 to 0.5 bar, via an additional permeable honeycomb- or grid-like intermediate layer, in the free spaces of which additional oxygen is available. Regarding the oxygen supply when compacting the material under pressure, the use of such a grid- or honeycomb-like intermediate layer as an aid for producing the material can also be provided in place of the cover layer which is to be bonded to the material. It is also possible to create a structure on the exterior of the material by means of the intermediate layer.

To prevent the adhesion of the finished material to the mold, a separating agent is advantageously distributed in the mold prior to filling the mixture in. If in the course of making the material without a cover layer, a grid- or honeycomb-like intermediate layer gets directly on the upper matrix layer, it is recommended to use a separating agent there, too, for preventing the adhesion of the polymerizing mixture or plastic material, and the same with all additional tools which come into contact with the polymerizing mixture.

The above described evening out and compacting of each individual matrix layer also results in air bubbles present in the mixture being pushed out, which otherwise would manifest themselves as hollow spaces or porous areas in the finished material. But it is even more effective if for this purpose the mixture is evacuated and thus practically completely vented prior to placing it in or on the mold.

The device for executing the described method has a mold for receiving the viscous mixture of the reaction components of the plastic material and a device for evening out and compacting the polymerizing mixture or the plastic material. Depending on the desired configuration of the material to be produced, the mold can be flat or curved or can have a complicated geometric shape; in general, flat material is produced, so that an also flat, plate-like mold is used.

The device for evening out and compacting has a bar which essentially is embodied complementary to the mold, i.e. straight or curved, and which can be displaced along the mold resting on the respectively last fed in matrix layer.

A particularly good effect is achieved when the edge of the bar provided for contact with the matrix layer is flexibly connected with the bar or consists of a flexible material, for example an elastic lip or an elongated brush.

To exert pressure on the upper matrix layer or the permeable cover layer, the device can have a pressure element which is embodied complementary to the mold or the material. In the most common case, i.e. for generating a level material, the pressure element is a plate which can be displaced crosswise to the material and can be pressed on the material. Although in general a pressure element is used which covers the entire forming material is used, it is also possible to work with a smaller pressure element—particularly when producing curved materials—which respectively only covers one area of the material and is pressed repeatedly against the material, so that all areas of the material are compacted sequentially.

The device can additionally have a honeycomb- or grid-like intermediate layer which can be placed on the material underneath the pressure element. The effect of this intermediate layer has already been explained. A suitable width of the honeycombs can be 0.5 cm, for example. Such an intermediate layer can also be used for creating a suitable surface structure of the material.

A plastic plate can be provided between the honeycomb- or grid-shaped intermediate layer and the pressure element.

The use of the novel material for producing orthopedic devices takes place in such a way that the material is heated until it is plastically deformable, which in connection with the pMMA mentioned is the case approximately at 170° C. to 180° C. This is followed by the required shaping of the material and its further processing, for example its connection with other components of the orthopedic device. If it is noted after shaping the material or in the course of an experimental use of the orthopedic device that a re-deformation is necessary, the material can be again heated to the temperature mentioned in a simple manner, for which a hot air blower is generally sufficient, after which a re-deformation can be performed. Re-deformation can take place in the same way when it is necessary to adapt the orthopedic device to an anatomical change which has taken place in the course of time.

The novel material can easily be deformed into curved surfaces; in this case the smallest possible radius of the curve is determined to a large extent by the rigidity of the fibers. A spherical deformation of the material, however, is only possible to a very limited degree. To produce spherically curved surfaces it is therefore generally necessary to provide the material with incisions. To determine whether and in what sizes to provide these incisions, it is possible to experimentally shape a fiber web of the same type as is used for insertion into the material in the same way as is provided for the material. If this fiber web can be deformed to the required extent, the material can be deformed to practically the same extent. Such a fiber web not embedded in plastic can therefore be used as a pattern for the material, so to speak.

If a material provided with a cover layer is used, it is necessary to remove this cover layer prior to shaping the material, which is possible in a simple way by pulling or tearing it off. Removal of the cover is made easier if it has a small tab projecting past the material layer, which can be grasped by an instrument or by hand. After removal of the cover layer a material is obtained having a surface free of dirt and minor damage. This surface is also slightly roughened so that it can be connected without difficulty with the other components of the orthopedic device by bonding without having to be ground or otherwise roughened prior to the application of the adhesive. It is of course also possible to connect the material by means of mechanical fastening devices with other components of orthopedic devices, for example with other plastics or metals.

BRIEF DESCRIPTION OF DRAWING

Some aspects of the invention will be further explained below by means of an exemplary embodiment, making reference to the drawings, wherein.

DETAILED DESCRIPTION OF EMBODIMENTS

Figure 1:
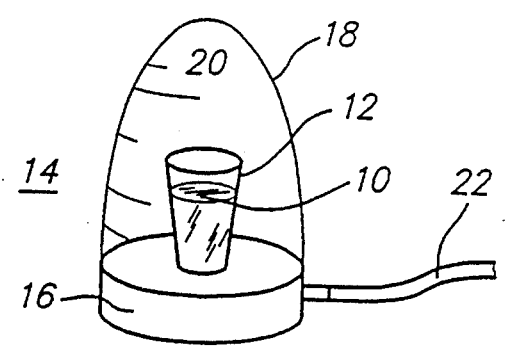
FIG. 1 shows the mixture of the reaction components of the plastic material in a vacuum installation.

In accordance with FIG. 1, a mixture 10 of reaction components of the plastic material intended for forming the matrix layers lies in a receptacle 12 which is located in a vacuum installation 14. This vacuum installation 14 has a base plate 16 and a bell 18 which together sealingly define a chamber 20. A line 22 is connected to this chamber 20 through which the drawn off gas flows out in the course of the evacuation of the chamber 20 by means of a pump, not shown.

To produce the preferably employed polymethyl methacrylate (PMMA), the following reaction components are used in the following composition:

Methyl methacrylate: 100 weight units

Hydroxypropionic acid: 0.5 weight units

Cyclohexanone peroxide mixture (for example Cyclonox LNC): 0.5 weight units

Vanadium monobutyl phosphite (for example VN2): 0.5 weight units

Cyclonox LNC and VN2 are products of AKZO Chemicals, but it is also possible to employ polymerization-triggering reaction components of other manufacturers.

Hydroxypropionic acid, Cyclonox LNC and VN2 are stirred sequentially into the methyl methacrylate. Since methyl methacrylate is not a Newtonian fluid, but instead is an intrinsically viscous liquid, a large amount of air becomes undesirably fed into the mixture during the mixing process which would result in the formation of bubbles or porous areas in the finished mixture, for which reason the mixture is evacuated as described above in the vacuum installation 14 to minimized air entrapment before being further used.

As already mentioned it is also possible to use amorphous thermoplastic materials, other than PMMA, e.g. PVC, polystyrene, styrene-butadiene interpolymer, styreneacrylonitrile interpolymer, polycarbonate, etc. so long as such amorphos thermoplastic material is sufficiently soft to permit reforming over a range of at least about 8° C. and also preferably has a softening temperature of less than 200° C.

Figure 2:
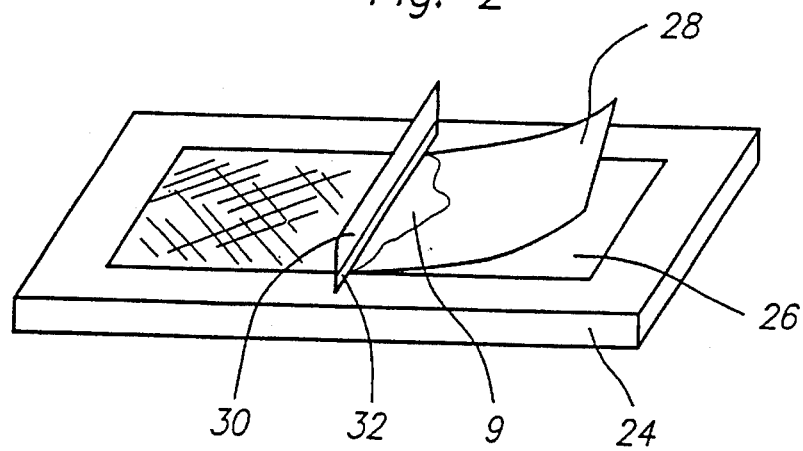
FIG. 2 is a simplified diagram of a portion of the device for producing the novel material wherein parts of the material are also visible.

FIG. 2 shows a plate-like mold 24; this can be a simple plastic mold, and in many cases disposable foam molds are sufficient.

Prior to applying the mixture 10, the mold 24 was treated with a separation agent, not shown, to prevent the adhesion of the mixture 10 or the plastic being made from it to the mold 24. Commercially available separating agents from the fiber-bonding technology are suitable for this.

Then the mixture 10, used for forming a matrix layer 26, was placed on the mold 24. FIG. 2 shows how subsequently tows or yarns of fibers 28 in the form of webs are placed on the matrix layer 26. The main direction of the fibers 28 is determined by the tensions to be absorbed in the use of the material being created. The fibers 28 are carbon fibers; however, fibers of other types can also be used as layments or in knitted or woven form.

Of the device for evening out and compacting the polymerized mixture 10, only a bar 30 is shown in FIG. 2, the edge of which, which touches the mixture 10, is formed by a flexible lip 32. The bar 30 is displaced under slight pressure over the fibers 28, the result of which is that a certain amount 9 of the mixture 10 reaches the surface of the web-shaped fibers 28. The tows or yarns of fibers 28 are embedded into the matrix layer 26 in this manner and are impregnated with the not yet polymerized plastic.

The process of creating such layers is repeated until the material 11 has been constructed, however, without a cover layer, from the desired number of matrix layers 26, respectively with inserted fibers 28, wherein the amorphous plastic holds the fibers of all layers together.

Figure 3:
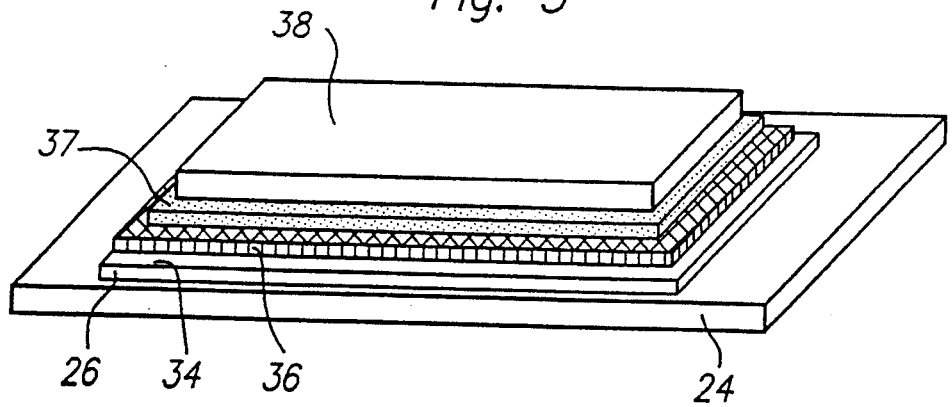
FIG. 3 is a simplified diagram of a further portion of the device of FIG. 2.

FIG. 3 illustrates how subsequently a permeable cover layer 34 in the form of a woven plastic material is placed on the uppermost matrix layer 26. This cover layer 34 is the last or uppermost of the layers of which the material 11 is composed.

Then compacting of the material 11 is performed under pressure. For this purpose, first a honeycomb—or grid-shaped intermediate layer 36 is placed on the material 11, which for example is made of aluminum or Aramid polymer and is approximately 1 cm thick and the top of which is connected with a plate 37 of foamed material. This plate protects a steel plate 38 acting as pressure element from damage by the honeycomb- or grid-like intermediate layer 36 and assures that the pressure is evenly exerted. The material 11 is compacted by the pressure of the steel plate 38 and the adhesion of the cover layer 34 on the uppermost one of the matrix layers 26 is achieved simultaneously. It is important that in the process oxygen, which is required for polymerization can reach the material from the ambient air thanks to the permeability of the cover layer 34 and the intermediate layer 36. Under suitable circumstances this can also be the case if no honeycomb- or grid-like intermediate layer 36 is used or when the cover layer 34 is omitted.

The mixture 10 is then polymerized at ambient temperature, so that it is possible after the time provided of approximately 8 hours to take the finished material 11 from the mold 24. For further deformation the material 11 is heated with simple means, for example a hot-air blower or within a hot cabinet, to approximately 170° C. to 180° C. and subsequently deformed. This deformation process can be repeatedly performed.

Figure 4:
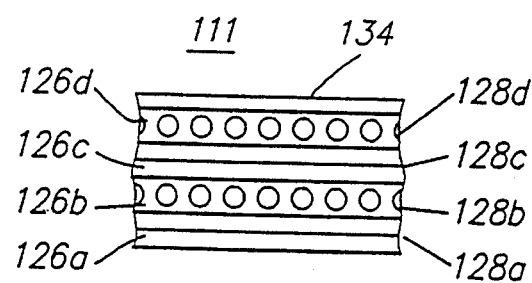
FIG. 4 is a sectional view of the novel material.

FIG. 4 schematically represents a section through a material 111 in accordance with the invention, which has been built up of four matrix layers 126a, 126b, 126c and 126d. Each one of these matrix layers is reinforced by a layer of inserted fibers 128a, 128b, 128c and 128d. The fibers 128a and 128c extend parallel to one another and crosswise to the parallel fibers 128b and 128d. By this arrangement the material can be highly stressed in two directions. An improved approximation of a two-dimensional, quasi isotropic material which can be stressed on all sides in the plane of the material is obtained, when the directions of the fibers of adjoining layers only diverge by 45 angular degrees in respect to each other.

A permeable cover layer 134 is applied to the uppermost matrix layer 126d and adheres to it and represents the outer layer of the material 111. This cover layer 134 is used for the supply of oxygen during polymerization, as protection of the uppermost matrix layer 126d before the material 111 is used and for providing a roughening of the uppermost matrix layer 128d when the cover layer 134 is removed, so that grinding of the material 111 prior to further processing by bonding can be omitted.

The above description relates to the production of a material in plate form. Materials of a slightly curved shape can be produced in the same way. However, if the material is intended to be produced as a complicated geometric structure, compacting of the individual laminate layers can take place by means of a bar which is flexible in the long direction, and compacting of the entire material by means of bandaging, for example with a woven nylon material.

The recited temperatures, pressures and times are a function of the plastic material of which the matrix layers are made. It should again be pointed out that polymerization temperatures of 20° C. to 25° C. are advantageous, because it is possible to work at room temperature. Furthermore, temperatures of less than 200° C. are advantageous for redeformation, because this temperature is achieved in a simple way, for example by means of a hot air blower.

The novel material is particularly suited for orthopedic devices and was particularly developed for making orthotic devices. However, it is also suitable for other self-supporting and in particular shell-shaped elements for orthopedic and other purposes, such a support surfaces, in particular for damaged body parts, or for supporting seat and/or back surfaces of seats, vehicle seats or wheelchairs which, thanks to the ability of the material to be re-deformed, can be adapted in situ with simple aids to the respective requirements of their user. In general, it can also be used in vehicle and aircraft construction, in space travel and for producing prototypes of different species.

The foregoing description of the specific embodiments will so fully reveal the general nature of the invention that others can, by applying current knowledge, readily modify and/or adapt for various applications such specific embodiments without departing from the generic concept, and, therefores such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A device for producing a material (11) adapted for use as an orthopedic article, made of at least one matrix layer (26) of thermoplastic material containing reinforcing fibers (28), and wherein the matrix layer (26) comprises an air-polymerizing, amorphous, thermoplastic material having a shear modulus (G) in its heat softened state of between 1 and 10 N/mm$^2$, the device comprising:

a mold (34) for receiving said matrix layer (26) and said reinforcing fibers (28), said mold having a base and sidewalls defining an upwardly open cavity for contacting a lower side of the material;

a scraper bar for evening out an upper side of the material and compacting the matrix layer, the bar being displaceable over the open cavity;

an air permeable intermediate layer (36) to be placed on the upper side of the material against an uppermost matrix layer; and means to compress the material while permitting access of oxygen to the material, comprising a pressure element (38) to be placed on the air permeable intermediate layer distal the uppermost matrix layer.

2. The device according to claim 1, wherein the scraper includes a deformable lip.

3. The device according to claim 2, wherein the deformable lip includes flexible material.

4. The device according to claim 2, wherein the deformable lip includes a brush.

5. The device according to claim 1, wherein the air permeable intermediate layer includes metallic or plastic honeycomb.

6. The device according to claim 1, comprising an oxygen supply providing 0.1 to 0.5 bar pressure.

7. The device according to claim 1, wherein the sidewalls define flat surfaces at their upper ends and the scraper bar extends over and is supported by the flat surfaces.

8. A device for producing a material (11) adapted for use as an orthopedic article, made of at least one matrix layer (26) of thermoplastic material containing reinforcing fibers (28), and wherein the matrix layer (26) comprises an air-polymerizing, amorphous, thermoplastic material having a shear modulus (G) in its heat softened state of between 1 and 10 N/mm², the device comprising:

a mold (34) for receiving said matrix layer (26) and said reinforcing fibers (28), said mold having a base and sidewalls defining an upwardly open cavity for contacting a lower side of the material;

an air permeable intermediate layer (36) to be placed on the upper side of the material against an uppermost matrix layer; and means to compress while permitting access of oxygen to the material, comprising a pressure element (38) to be placed on the air permeable intermediate layer distal the uppermost matrix layer.

9. The device according to claim 8, wherein the air permeable intermediate layer includes metallic or plastic honeycomb.

10. The device according to claim 8, comprising an oxygen supply providing 0.1 to 0.5 bar pressure.

11. A device for producing a material (11), for orthopedic articles, made of a matrix layer (26) of plastic with reinforcing fibers (28), the device comprising:

a mold (34) with an area for receiving a mixture (10) of reaction components to make an amorphous, thermoplastic material to form the matrix layer, with the fibers (28) placed on the matrix layer, and with a border area;

means for evening out the mixture (10) with a bar (30) being deplaceable along the border area of the mold (34) on the respectively last applied layer of the mixture (10), the bar (30) comprising a flexible lip (32) or brush, the lip or brush comprising an edge of the bar (30) to be in contact with the mixture (10); and means for compacting the mixture prior to polymerization comprising a pressure element (38) which can be pressed against the outermost layer of the material (11) and a permeable layer (34 or 36) which is placed underneath the pressure element (38) on the outermost laminate layer.

* * * * *